United States Patent
Lalonde

(10) Patent No.: US 9,168,079 B2
(45) Date of Patent: Oct. 27, 2015

(54) METHOD AND SYSTEM TO PREVENT COMPLETE OBSTRUCTION IN CATHETER IN CASE OF A KINK

(75) Inventor: Jean-Pierre Lalonde, Candiac (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 874 days.

(21) Appl. No.: 12/978,701

(22) Filed: Dec. 27, 2010

(65) Prior Publication Data

US 2012/0165802 A1    Jun. 28, 2012

(51) Int. Cl.
  *A61B 18/02* (2006.01)
  *A61B 18/00* (2006.01)
  *A61M 25/00* (2006.01)

(52) U.S. Cl.
  CPC ....... *A61B 18/02* (2013.01); *A61B 2018/00166* (2013.01); *A61B 2018/00214* (2013.01); *A61B 2018/00255* (2013.01); *A61B 2018/00791* (2013.01); *A61B 2018/0212* (2013.01); *A61B 2018/0262* (2013.01); *A61M 2025/0059* (2013.01)

(58) Field of Classification Search
  USPC ..................................................... 606/20–26
  See application file for complete search history.

(56) References Cited

U.S. PATENT DOCUMENTS

| | | | |
|---|---|---|---|
| 4,985,022 A | | 1/1991 | Fearnot et al. |
| 5,460,608 A | * | 10/1995 | Lodin et al. .............. 604/103.09 |
| 5,507,301 A | * | 4/1996 | Wasicek et al. ................ 600/585 |
| 5,624,392 A | * | 4/1997 | Saab ............................... 604/43 |
| 5,782,811 A | | 7/1998 | Samson et al. |
| 5,891,112 A | * | 4/1999 | Samson .......................... 604/524 |
| 6,270,476 B1 | * | 8/2001 | Santoianni et al. ......... 604/95.04 |
| 6,270,493 B1 | * | 8/2001 | Lalonde et al. .................. 606/23 |
| 6,514,245 B1 | * | 2/2003 | Williams et al. ................ 606/21 |
| 6,620,149 B1 | | 9/2003 | Lenz et al. |
| 2001/0049547 A1 | | 12/2001 | Moore |
| 2002/0045893 A1 | | 4/2002 | Lane et al. |
| 2003/0171742 A1 | | 9/2003 | Mihalik et al. |

FOREIGN PATENT DOCUMENTS

| | | |
|---|---|---|
| EP | 0435518 A1 | 3/1991 |
| WO | 9625969 | 8/1996 |
| WO | 0182810 | 11/2001 |
| WO | 0182810 A1 | 11/2001 |

* cited by examiner

*Primary Examiner* — Michael Peffley
(74) *Attorney, Agent, or Firm* — Christopher & Weisberg, P.A.

(57) ABSTRACT

A medical device comprising a shaft having a kink radius; a tube disposed within the shaft; a fluid source in fluid communication with the tube; an elongate member disposed within the tube, and the elongate member imparting a kink radius on the tube, the imparted kink radius of the tube being larger than the kink radius of the shaft.

15 Claims, 4 Drawing Sheets

Section A-A

METHOD AND SYSTEM TO PREVENT COMPLETE OBSTRUCTION IN CATHETER IN CASE OF A KINK

CROSS-REFERENCE TO RELATED APPLICATION

Not Applicable.

STATEMENT REGARDING FEDERALLY SPONSORED RESEARCH OR DEVELOPMENT

Not Applicable.

FIELD OF THE INVENTION

The present invention relates to catheters used in medical procedures, and more particularly to catheters that resist partial or complete obstruction in the case of a kink during use.

BACKGROUND OF THE INVENTION

Many medical procedures are performed using minimally invasive surgical techniques, wherein one or more slender implements are inserted through one or more small incisions into a patient's body. Catheters are increasingly used to access remote regions of the human body to deliver diagnostic or therapeutic agents or for the treatment of biological tissue. Catheters which use the cardiovascular system as the pathway to a treatment site, for example, are especially practical.

In many applications, the catheter delivers therapeutic agents or applies energy-based principles to the tissue based on the transfer of fluid through the catheter. In tissue ablation, for example, the surgical implement is a catheter that can include a rigid or flexible structure having an ablation device at or near its distal end that is placed adjacent to the tissue to be ablated. Radio frequency energy, microwave energy, laser energy, extreme heat, and extreme cold can be provided by the ablation device to ablate the tissue. In other applications, regional anesthesia can be applied by using such surgical instruments. In still other applications, diagnostic or therapeutic agents can be delivered to a treatment site by way of a catheter.

Often the treatment area which one desires to access by catheter is within a soft or muscular tissue such as the liver, brain, veins and arteries, biliary ducts or ostia, or the heart. These are difficult sites to reach. The catheter must be introduced through a biological cavity, for example, a large artery such as those found in the groin or the neck and then be passed through narrowing regions of the cardiovasculature until the catheter tip reaches the selected site. Often such biological passageways wind and loop or are otherwise tortuous. Catheters for such applications are difficult to design, since they must be fairly stiff at their proximal end to allow passage of the catheter tip through the loops and increasingly smaller passageways and at the same time not cause significant trauma to the passageway and further be flexible enough to navigate the passageway.

Examples of catheters designed to meet these criteria are disclosed in the art. Often, the catheter shaft is made with a flexible material to permit it to navigate the passageway used to reach a treatment site. Since many catheter-based applications involve the transmission of a therapeutic agent or fluid from the catheter's proximal to distal end for applications at the treatment site, the shaft of the catheter often has internal lumens that permit the delivery or return of a particular therapeutic agent or fluid. For example, cryosurgery catheters have internal lumens that deliver refrigerant to the catheter tip for treatment and exhaust the refrigerant from the tip. Owing to the properties of the catheter that make it flexible, however, kinks may still form in the catheter shaft during use when the shaft is bent beyond its minimum bend radius or kink radius.

Solutions advanced in the catheter arts generally place metal braids or wires at the outer wall of the catheter shaft to reduce the likelihood of a kink forming. But such catheters still kink when the catheter is bent beyond its kink radius during use. When a kink forms in the catheter shaft during use, the passage, or the internal lumens within the shaft, can become obstructed, and the flow of a therapeutic agent or fluid can be interrupted.

It is therefore desirable to provide a device that resists or prevents such kink-related obstructions and interruptions in fluid or agent delivery.

SUMMARY OF THE INVENTION

The present invention advantageously provides a medical device comprising a shaft having a kink radius; a tube disposed within the shaft; a fluid source in fluid communication with the tube; an elongate member disposed within the tube, and the elongate member imparting a kink radius on the tube, the imparted kink radius of the tube being smaller than the kink radius of the shaft.

A medical device is also provided, including a catheter having a kink radius; a conduit coaxial with and disposed within the catheter, the conduit defining a lumen; a cryogenic fluid source in fluid communication with the conduit; a rod disposed within the lumen and affixed to one end of the conduit, and the rod imparting a kink radius on the conduit, the imparted kink radius of the conduit being smaller than the kink radius of the catheter.

A medical device is also provided, including a catheter body; a fluid injection tube coaxial with and disposed within the catheter body; a fluid exhaust lumen coaxial with and defined by the catheter body; a cryogenic fluid source in fluid communication with the fluid injection tube; an expandable element in fluid communication with the fluid injection tube; and a rod disposed within at least a portion of the fluid injection tube.

A medical device is also provided, a cryogenic medical device comprising a shaft having a kink radius; a tube disposed within the shaft; a fluid source in fluid communication with the tube; and an elongate member disposed within the tube, the elongate member being substantially resilient and maintaining its shape when a kink occurs to prevent the kink from obstructing the tube.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
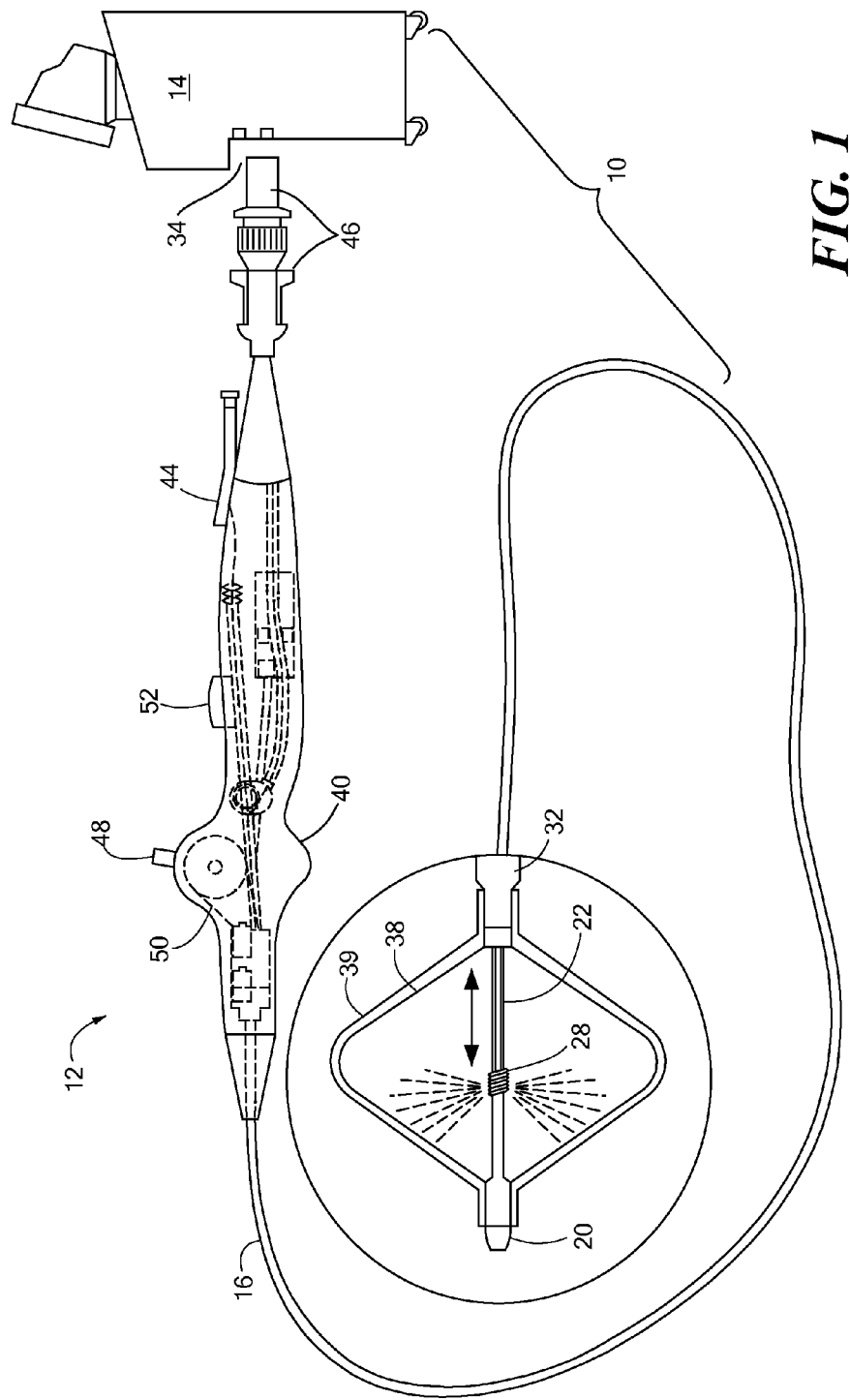
FIG. 1 is an illustration of an embodiment of a medical system constructed in accordance with the principles of the present invention.

The present invention advantageously provides a method and system for preventing partial or complete obstruction of fluid flow within a kinked catheter body. Referring now to the drawing figures in which like reference designations refer to like elements, an embodiment of a medical system constructed in accordance with principles of the present invention is shown in FIG. 1 and generally designated as "10." The system 10 generally includes a medical device 12 that may be coupled to a coolant control and delivery system 14. The medical device 12 may generally include one or more treatment regions for energetic or other therapeutic interaction between the medical device 12 and a treatment site. The treatment region(s) may deliver, for example, cryogenic therapy, radiofrequency energy, or other energetic transfer with a tissue area in proximity to the treatment region(s), including cardiac tissue.

Continuing to refer to FIG. 1, the medical device 12 may include an elongate body 16 passable through a patient's vasculature and/or proximate to a tissue region for diagnosis or treatment, such as a catheter, sheath, or intravascular introducer. The elongate body 16 may define a proximal portion 18 and a distal portion 20, and may further include one or more lumens disposed within the elongate body 16 thereby providing mechanical, electrical, and/or fluid communication between the proximal portion of the elongate body 16 and the distal portion of the elongate body 16, as discussed in more detail below.

The medical device 12 may include a shaft 22 at least partially disposed within a portion of the elongate body 16. The shaft 22 may extend or otherwise protrude from a distal end of the elongate body 16, and may be movable with respect to the elongate body 16 in longitudinal and rotational directions. That is, the shaft 22 may be slidably and/or rotatably moveable with respect to the elongate body 16. The shaft 22 may further define a lumen therein for the introduction and passage of a guide wire. The shaft 22 may include or otherwise be coupled to a distal tip that defines an opening and passage therethrough for the guide wire.

The medical device 12 may further include a fluid injection tube 28 traversing at least a portion of the elongate body 16 and towards the distal portion 20. The injection tube 28 may be coupled to or otherwise extend from the distal portion of the elongate body 16, and may further be coupled to the shaft 22 and/or distal tip of the medical device 12. The fluid injection tube 28 may be flexible, constructed from a shape memory material (such as Nitinol), and/or include other controllably deformable materials that allow the fluid injection tube 28 to be manipulated into a plurality of different geometric configurations, shapes, and/or dimensions.

The fluid injection tube 28 may define a lumen therein for the passage or delivery of a fluid from a fluid source, for example, cryogenic fluid. The fluid injection tube 28 may further include one or more apertures or openings therein to provide for the dispersion or directed ejection of fluid from the tube 28 to an environment exterior to the fluid injection tube 28. The fluid injection tube 28 may further define a coil or a helical shape towards the distal end of the medical device 12 with the fluid injection tube 28 defining the one or more apertures around the helix.

Figure 2:
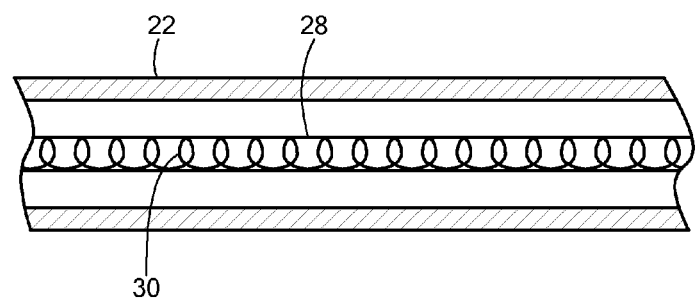
FIG. 2 is a side cross-sectional view of a medical device constructed in accordance with the principles of the present invention showing a coiled elongate member.

Referring now to FIG. 2, the fluid injection fluid injection tube 28 may be composed of materials that better resist kinking, for example, plastics, such as polyimide or polyamide, nylon, silicon, or polymers. The fluid injection tube 28 may also be composed of materials that resist cracking, corrosion, or deterioration such that a cryogenic fluid, for example, nitrogen, argon, or mixtures thereof may flow through the fluid injection tube 28. Alternatively, the fluid injection tube 28 may be composed of materials to accommodate fluids such as saline, chilled or heated liquids, and or gases.

The diameter and thickness of fluid injection tube 28 may vary depending on the diameter of the elongate body 16, the type of medical procedure performed, the type of fluid circulating through the fluid injection tube 28, and where the elongate body 16 is positioned in the body. For example, the fluid injection tube 28 may have a diameter to length ratio of 0.025 such that the fluid pressure within the injection lumen 28 is sufficient to deliver cryogenic fluid toward the distal end of the medical device 12.

Continuing to refer to FIG. 2, an elongate member 30 may be disposed within the fluid injection tube 28 operable to prevent the fluid injection tube 28 from kinking when a kink is formed in the shaft 22. The elongate member 30 may be a tubular or solid wire or rod composed of plastic, nylon, polyimide, polyamide, and the like; or a metal, such as copper, stainless steel, or any alloy such as nitinol (which can return to an initial shape); or a thermoplastic or thermoelastic material that is resilient and flexible. The elongate member 30 defines a kink radius or otherwise imparts a kink radius when combined with the fluid injection tube 28 that is smaller than a kink radius defined by the shaft 22. As used herein, the phrase "kink radius" means the minimum radius or diameter of curvature which can be imposed on a tubular structure without causing a kink in the longitudinal axis of its wall. The smaller the kink radius, the greater the kink resistance.

The elongate member 30 may be anchored or otherwise coupled to the proximal and/or distal end of the medical device 12. For example, the elongate member 30 may extend through the fluid injection tube 28 and terminate either proximate the helical portion of the fluid injection 28 or terminate at the distal end of the helical portion, such that it defines a helical shape within the helical portion. The elongate member 30 may extend through any desired length or segment of the fluid injection tube 28. For example, the elongate member 30 may traverse substantially the entire length of the fluid injection tube 28 or may traverse a portion of the fluid injection tube 28 having a greater likelihood of exposure to kinks or bending forces or an increased susceptibility to kinking, such as a junction or threshold in the medical device where components, materials or portions thereof have different bending behavior or characteristics. The elongate member 30 may further be linear, curvilinear, or define a coil or any number of shapes when disposed within the fluid injection tube 28. For example, the elongate member 30 may unfold, coil, or otherwise define a variety of prefabricated shapes when disposed within the fluid injection tube 28. For example, the elongate member 30 is substantially linear when disposed within fluid injection tube 28 before entry into the vasculature. Upon entry into the vasculature, the temperature of the elongate member 30 increases and the elongate member 30 may form a coil such that it imparts a radial force on the wall of the fluid injection tube 28.

The elongate member 30 may further define a width such that a pressure or flow rate of a circulating fluid within fluid injection tube 28 is minimally affected by the disposition of elongate member 30 within the fluid injection tube 28. The width of the elongate member 30 may be uniform or variable within the fluid injection tube 28. For example, the elongate member 30 may be wider or smaller width at different longitudinal positions within the fluid injection tube 28, which may depend on where the fluid injection tube 28 is flexed or torqued such that increased resistance to kinking is provided at those positions. In a particular configuration where the elongate member 30 is a substantially linear elongated rod, the rod may define an outer diameter equal to approximately 50% of the diameter of the fluid flow area of the fluid injection tube 28, or the inner diameter of the fluid injection tube 28. In such a configuration, the cross-sectional area of flow of fluid through the fluid injection tube would only be reduced by about 25% compared to the cross-sectional area of the fluid injection tube 28 with no rod. As such, a larger rod may be placed inside the fluid injection tube without a significant decrease in fluid flow through the fluid injection tube 28. In a configuration where the rod is stainless steel and has an outer diameter that is 50% of the diameter of the fluid flow cross-sectional diameter of the fluid injection tube 28, the probability of a kink in the shaft 22 causing a kink in the fluid injection tube 28 is very low.

The elongate member 30 may further be positioned within the fluid injection tube 28 to be substantially coaxial with fluid injection tube 28 or alternatively contour the inner wall of the fluid injection tube 28. Optionally, additional elongate members 30 may be disposed within the fluid injection tube 28 to increase the kink resistance of the fluid injection tube 28. For example, one elongate member 30 may be disposed at substantially the center of the fluid injection tube 28 and a second rod may be disposed radially around the inner wall of fluid injection tube 28. It is further contemplated that the elongate member 30 may be independently controlled, such that its position and disposition with the fluid injection tube 28 can be modified for a designated procedure. For example, the elongate member 30 may be independently movable and/or slidable within the fluid injection tube 28 in any plane and along any axis through the use of one or more steering wires or other actuators coupled to the elongate member 30 and accessible to a user or physician at the proximal end or handle portion of the device.

Figure 3:
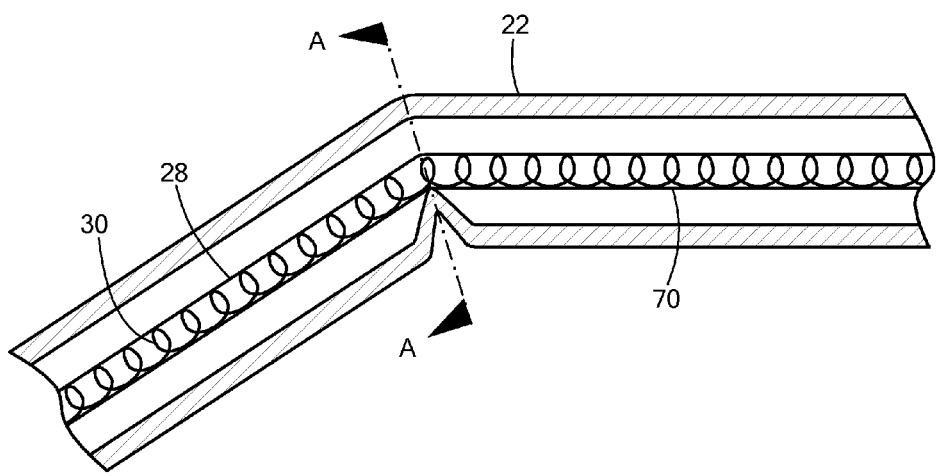
FIG. 3 is side cross-sectional view of the medical device shown in FIG. 2 with a kink.
Figure 4:
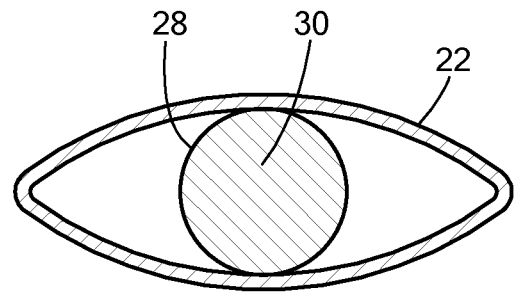
FIG. 4 is a cross-sectional view of section A-A in FIG. 3.

Now referring to FIGS. 3 and 4, a local kink in the shaft 22 may cause the diameter of the shaft 22 to decrease, which can affect the local or systematic fluid flow rate within the shaft 22. A kink may generally occur in any plane and in any location along the perimeter of the shaft 22 during its use. Accordingly, the inner wall of the shaft 22 may impact and affect the fluid injection tube 28 at any angle and with varying force. Because the elongate member 30 imparts a smaller kink radius on the fluid injection tube 28 compared to the kink radius of the shaft 22, a kink in the shaft 22 either does not cause a kink in the fluid injection tube 28 or does not cause a kink resulting in complete obstruction in the fluid injection tube 28 sufficient to impede and/or cause a drop in the fluid flow rate toward the distal end of the medical device 12 and/or prevent the pressure transmission. For example, depending on the medical device 14, the maximum bending force applied to the shaft 22 may be less than the minimum force necessary to kink the fluid injection tube 28. As such, patency is maintained within the fluid injection tube 28 when a kink occurs in the shaft 22. Further, the elongate member 30 may be disposed within an additional tube (not shown) disposed within the shaft 22. The additional tube may include one or more pressure sensors at its distal end operable to sense pressure changes during treatment. In such a configuration, the elongate member 30 prevents a complete kink in the Sniffer tube such that pressure does not build up at either proximal or distal to the kink.

Continuing to refer to FIGS. 3 and 4, during a cryogenic ablation procedure where cryogenic fluid in liquid phase is circulated through the fluid injection tube 28 toward the distal end of the medical device 12, the fluid may be circulated at a high pressure, for example 500 to 760 psig. The liquid cryogenic fluid may then be expanded by the Joule-Thomson effect, change phase into a gas, and exhausted out through an exhaust lumen 32 at low pressure, for example 10 pisa to 55 psia. A kink in the fluid injection tube 28 during this ablation procedure may increase the pressure drop at the kink location and decrease the fluid flow at the distal end of the medical device 12. In response to the drop in flow at the distal end of the medical device 12, the delivery system 14, discussed in more detail below, may increase the inlet pressure to compensate for the drop in flow in order to maintain a constant delivery of cryogenic fluid. Should this happen when the fluid injection tube 28 is kinked, the pressure buildup proximate the kink may overcome the structural integrity of the fluid injection tube 28 and the shaft 22 such that the elongate body 16 ruptures or explodes. As such, the placement and positioning of the elongate member 30 within the fluid injection tube 28 overcomes the drawbacks of placing a braid within the wall of the shaft 22, or within, for example, the exhaust lumen 32, the placement of which fails to keep the fluid flowing at a constant rate during a kink.

Figure 5:
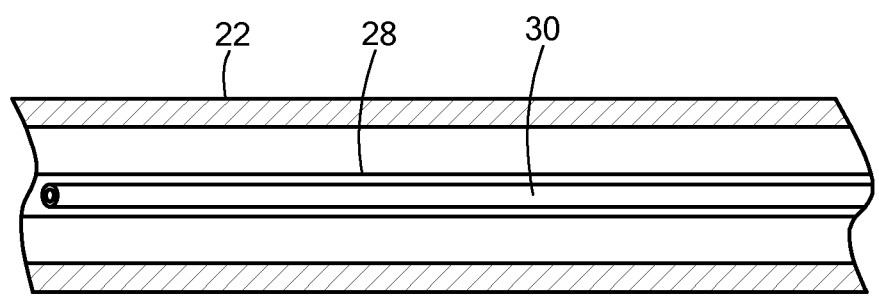
FIG. 5 is a side cross-sectional view of a medical device constructed in accordance with the principles of the present invention showing a substantially linear elongate member.

For example, the elongate member 30 may be a tubular or solid rod defining a coil, or a substantially linear structure coaxial with the lumen of the fluid injection 28, as shown in FIG. 5. In either configuration, the rod is disposed within the fluid injection tube 28 such that in the presence of a kink a smaller diameter of fluid injection tube 28 remains open for passage of fluid. Although, a small pressure drop in fluid flow rate occurs at the kink location, the overall fluid flow rate within the fluid injection tube 28 may remain substantially unaffected, thus minimizing the impact of local kinks in the fluid injection tube 28.

Referring back now to FIG. 1, the system may generally include a control unit or console 34 coupled to the medical device 12 and/or delivery system 14. The console 34 may also include one or more sensors to monitor the operating parameters throughout the system, including for example, pressure, temperature, flow rates, volume, or the like. The medical device may further include a thermal treatment region 36 at or near the distal portion of the device. The thermal treatment region 36 may include a thermally-transmissive section or area allowing thermal exchange with a targeted tissue or region external to the medical device using one or more thermal treatment modalities, such as radiofrequency energy delivery, cryogenic treatment of the tissue for example. As shown in FIG. 1, the thermal treatment region 36 may include an expandable element 38 at the distal portion of the elongate body 16. The expandable element 38 may be coupled to a portion of the elongate body 16 and also coupled to a portion of the shaft 22 and/or distal tip 26 to contain a portion of the fluid injection tube 28 therein. The expandable element 38 defines an interior chamber or region that contains coolant or fluid dispersed from the fluid injection tube 28, and may be in fluid communication with the exhaust lumen 32 defined by or included in the elongate body 16 for the removal of dispersed coolant from the interior of the expandable element 38. The expandable element 38 may further include one or more material layers providing for puncture resistance, radiopacity, or the like. Of note, while the thermal treatment region 36 is described as including an expandable element 38, other configurations of the thermal treatment region are contemplated, including linear thermal segments, arcuate thermal segments, non-expandable cooling chambers, and the like. Optionally, a second expandable element 39 may be included on the elongate body 16, the second expandable element surrounding the expandable element 38, such that a safety space under a vacuum is defined between the expandable element 38 and the second expandable element 39. Should a leak occur, fluid may egress into the safety space where fluid may be exhausted.

Figure 6:
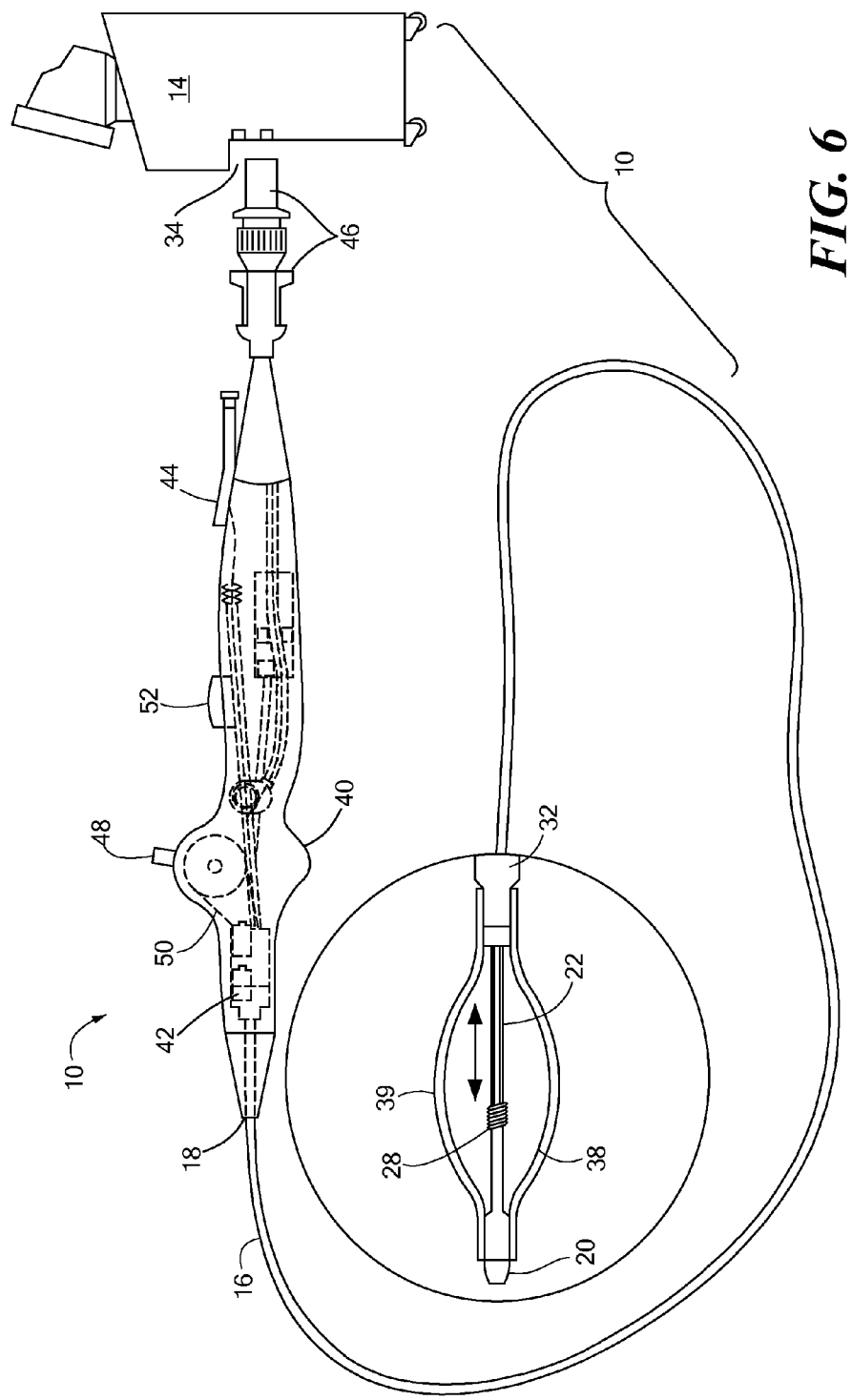
FIG. 6 is an illustration of an embodiment of the medical system shown in FIG. 1 with the expandable element in a deflated state.

Now referring to FIG. 6, in an embodiment where the medical device 12 includes an expandable element 38, expansion of the expandable element 38 may exert pressure on the shaft 22 and the fluid injection tube 28 in the longitudinal and radial directions. In particular, as shown in FIGS. 1 and 6, as the expandable element 38 expands it longitudinally displaces and portion of the shaft 22 and the fluid injection tube 28 connected to the shaft. This may cause a kink in the shaft 22 and/or the fluid injection tube 28 when positioned within the expandable element 38 or at a position proximal to the expandable element 38, particularly when the shaft 22 is composed of soft materials such as polyamide and polyimide. Placement of the elongate member 30 within the fluid injection tube 28 minimizes the risk of fluid flow obstruction in such a configuration.

The medical device 12 may include a handle 40 coupled to the proximal portion of the elongate body 16. The handle 40 can include circuitry for identification and/or use in controlling of the medical device 12 or another component of the system. For example, the handle 40 may include one or more pressure sensors 42 to monitor the fluid pressure within the medical device 12. Additionally, the handle 40 may be provided with a fitting 44 for receiving a guide wire that may be passed into the guide wire lumen 24. The handle 40 may also include connectors 46 that are matable to the coolant control and delivery system 14 either directly or indirectly by way of one or more umbilicals. The handle 40 may further include blood detection circuitry in fluid and/or optical communication with the injection, exhaust and/or interstitial lumens. The handle 40 may also include a pressure relief valve in fluid communication with the fluid injection tube 28 and/or exhaust lumen 32 to automatically open under a predetermined threshold value in the event that value is exceeded.

The handle 40 may also include one or more actuation or control features that allow a user to control, deflect, steer, or otherwise manipulate a distal portion of the medical device from the proximal portion of the medical device. For example, the handle 40 may include one or more components such as a lever or knob 48 for manipulating the elongate body 16 and/or additional components of the medical device 12, such as a pull wire 50 with a proximal end and a distal end anchored to the elongate body 16 at or near the distal portion. The medical device 12 may include an actuator element 52 that is movably coupled to the proximal portion of the elongate body 16 and/or the handle 40. The actuator element 52 may further be coupled to a proximal portion of the shaft 22 such that manipulating the actuator element 52 in a longitudinal direction causes the shaft 22 to slide towards either of the proximal or distal portions of the elongate body 16. The actuator element 52 may include a thumb-slide, a push-button, a rotating lever, or other mechanical structure for providing a movable coupling to the elongate body 16, the handle 40, and/or the shaft 22. Moreover, the actuator element 52 may be movably coupled to the handle 40 such that the actuator element is movable into individual, distinct positions, and is able to be releasably secured in any one of the distinct positions.

The system 10 may further include one or more sensors to monitor the operating parameters throughout the system, including for example, pressure, temperature, flow rates, volume, or the like in the coolant control and delivery system 14 and/or the medical device 12, in addition to monitoring, recording or otherwise conveying measurements or conditions within the medical device 12 or the ambient environment at the distal portion of the medical device 12. The sensor(s) may be in communication with one or more components of the coolant control and delivery system 14 for initiating or triggering one or more alerts or therapeutic delivery modifications during operation of the medical device 12. One or more valves, controllers, or the like may be in communication with the sensor(s) to provide for the controlled dispersion or circulation of fluid through the lumens/fluid paths of the medical device 12. Such valves, controllers, or the like may be located in a portion of the medical device 12 and/or in the coolant control and delivery system 14, as described in more detail below.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device comprising:
    a shaft having a kink radius;
    a tube disposed within the shaft, the tube defining a lumen having an inner surface a diameter;
    a fluid source in fluid communication with the tube lumen; and
    a coiled elongate member disposed within the tube lumen and at least a portion of the coiled elongate member being in contact with the inner surface of the tube, the coiled elongate member having an outer diameter that is less than the diameter of the tube lumen, the coiled elongate member being coaxial with the tube and imparting a kink radius on the tube, the imparted kink radius of the tube being smaller than the kink radius of the shaft.

2. The medical device of claim 1, wherein the coiled elongate member traverses only a portion of the tube.

3. The medical device of claim 1, wherein the coiled elongate member is affixed to the proximal end of the tube.

4. The medical device of claim 1, wherein the coiled elongate member is comprised of a shape memory material.

5. The medical device of claim 1, further comprising a guide wire disposed within the shaft.

6. The medical device of claim 1, further including an expandable element in fluid communication with the tube.

7. The medical device of claim 1, wherein the fluid source is a cryogenic fluid.

8. A cryogenic medical device comprising:
    a catheter having a kink radius;
    a conduit coaxial with and disposed within the catheter, the conduit defining a lumen having an inner surface and a diameter;
    a cryogenic fluid source in fluid communication with the conduit lumen; and
    a coiled rod disposed within the conduit lumen and affixed to the proximal end of the conduit, at least a portion of the coiled rod being in contact with the inner surface of the lumen, the coiled rod having an outer diameter that is less than the diameter of the conduit lumen, the coiled rod being coaxial with the tube and imparting a kink radius on the conduit, the imparted kink radius of the conduit being smaller than the kink radius of the catheter.

9. The medical device of claim 8, further comprising an expandable element in fluid communication with the conduit.

10. The medical device of claim 8, further comprising a guidewire disposed within the catheter.

11. The medical device of claim 8, wherein an outer diameter of the coiled rod is about half of an inner diameter of the conduit.

12. The medical device of claim 8, wherein the coiled rod is a first rod, the device further comprising a second rod disposed within the conduit.

13. The medical device of claim 12, wherein the second rod imparts a kink radius on the conduit.

14. A cryogenic medical device comprising:
a catheter body defining a kink radius;
a fluid injection tube coaxial with and disposed within the catheter body, the fluid injection tube defining an inner diameter and having an inner surface;
a fluid exhaust lumen coaxial with and defined by the catheter body;
a cryogenic fluid source in fluid communication with the fluid injection tube;
an expandable element in fluid communication with the fluid injection tube; and
a coiled rod coaxially disposed within at least a portion of the fluid injection tube, the coiled rod defining an outer diameter that is approximately equal to half of the inner diameter of the fluid injection tube, at least a portion of the coiled rod being in contact with the inner surface of the fluid injection tube.

15. A cryogenic medical device comprising:
a shaft having a kink radius;
a tube disposed within the shaft, the tube defining a lumen having an inner diameter and an inner surface;
a fluid source in fluid communication with the tube lumen; and
a coiled elongate member disposed within the tube lumen such that at least a portion of the coiled elongate member is in contact with the inner surface of the tube, the coiled elongate member having an outer diameter that is smaller than the inner diameter of the tube lumen, the coiled elongate member being substantially resilient and maintaining its shape when a kink occurs to prevent the kink from obstructing the tube.

* * * * *